US007767422B2

(12) United States Patent
Kopreski et al.

(10) Patent No.: US 7,767,422 B2
(45) Date of Patent: *Aug. 3, 2010

(54) DETECTION OF 5T4 RNA IN PLASMA AND SERUM

(75) Inventors: Michael S. Kopreski, Long Valley, NJ (US); Christopher D. Gocke, Ellicott City, MD (US)

(73) Assignee: Oncomedx, Inc., Long Valley, NJ (US)

( * ) Notice: Subject to any disclaimer, the term of this patent is extended or adjusted under 35 U.S.C. 154(b) by 700 days.

This patent is subject to a terminal disclaimer.

(21) Appl. No.: 10/363,023

(22) PCT Filed: Aug. 21, 2001

(86) PCT No.: PCT/US01/26119

§ 371 (c)(1),
(2), (4) Date: Jul. 17, 2003

(87) PCT Pub. No.: WO02/18645

PCT Pub. Date: Mar. 7, 2002

(65) Prior Publication Data

US 2004/0014079 A1    Jan. 22, 2004

Related U.S. Application Data

(63) Continuation-in-part of application No. 09/649,371, filed on Aug. 28, 2000, now Pat. No. 6,794,135, which is a continuation-in-part of application No. 09/155,152, filed on Sep. 22, 1998, now Pat. No. 6,329,179.

(51) Int. Cl.
*C12P 19/34*  (2006.01)
*C12Q 1/68*   (2006.01)
*C07H 21/02*  (2006.01)
*C07H 21/04*  (2006.01)
*C07H 21/00*  (2006.01)

(52) U.S. Cl. .................. 435/91.2; 435/6; 435/91.1; 435/91.51; 536/23.1; 536/24.3; 536/24.33; 536/25.3

(58) Field of Classification Search .................. 435/6, 435/91.1, 91.2, 91.51, 183; 436/94; 536/23.1, 536/24.3, 24.33, 25.3, 25.32
See application file for complete search history.

(56) References Cited

U.S. PATENT DOCUMENTS

| | | | | |
|---|---|---|---|---|
| 5,576,178 A | * | 11/1996 | Emanuel et al. | .................. 435/6 |
| 5,869,053 A | * | 2/1999 | Stern et al. | ............... 424/184.1 |
| 5,939,262 A | * | 8/1999 | Pasloske et al. | .................. 435/6 |
| 6,258,540 B1 | | 7/2001 | Lo et al. | |
| 6,329,179 B1 | | 12/2001 | Kopreski | |
| 6,664,056 B2 | | 12/2003 | Lo et al. | |
| 6,794,135 B1 | * | 9/2004 | Kopreski et al. | .................. 435/6 |
| 6,916,634 B2 | * | 7/2005 | Kopreski | .................... 435/91.2 |
| 6,939,671 B2 | * | 9/2005 | Kopreski | .................. 435/6 |

| | | | |
|---|---|---|---|
| 2004/0203037 A1 | * | 10/2004 | Lo et al. .................. 435/6 |

FOREIGN PATENT DOCUMENTS

| | | |
|---|---|---|
| DE | 3717212 | 9/2003 |
| EP | 0336562 A | 10/1989 |
| WO | WO 90/09456 A1 | 8/1990 |
| WO | WO 97/35589 A | 10/1997 |

OTHER PUBLICATIONS

Southall et al., A 72 kD trophoblast glycoprotein defined by a monoclonal antibody. British Journal of cancer, 57, 239-246, 1988.*
Hole et al., Immunohistological distribution of 5T4 antigen in normal and malignant tissues. British Journal of cancer, 61, 89-95, 1990.*
Rykova et al., Concentration of circulating RNA from healthy donors and cancer patients estimated by different methods. Ann. N.Y. Acad. Sci., 1075, 328-333, 2006.*
Attached definition for gestational trophoblastic disease.*
Kopreski et al., Circulating RNA as a tumor marker: Detection of 5T4 mRNA in breast and lung cancer patient serum. Ann. N.Y. Acad. Sci., 945, 172-178, 2001.*
Guin et al., Electrophoretic characterization of plasma RNA. Biochemical Medicine, 13, 224-230, 1975.*
The definitions for "extracellular" and "intracellular" from Wikipedia, the free encyclopedia. Printed on May 15, 2009.*
Hasselmann et al., "Detection of Tumor-Associated circulating mRNA in serum, plasma and blood cells from patients with disseminated malignant melanoma," *Oncology Reports*, 2001, 8:115-118.
Kopreski et al., "Detection of Tumor Messenger RNA in the Serum of Patients with Malignant Melanoma", *Clinical Cancer Research*, Aug. 1999, 5:1961-1965.
Komeda et al., "Sensitive Detection of Circulating Hepatocellular Carcinoma Cells in Peripheral Venous Blood", *Cancer* 1995, 75: 2214-2219.
Pfleiderer et al., "Detection of Tumor Cells in Peripheral Blood and Bone Marrow from Ewing Tumour Patients by Rt-PCR," *Int. J. Caner (Red. Oncol.)* 1995, 64: 135-139.
King et al.,"Organization of the mouse and human 5T oncofoetal leucine-rich glycoprotein genes and expression in foetal and adult murine tissues", Biochimica et Biophysica Acta. Gene Structure and Expression, Elsevier, Amsterdam, NL, vol. 1445, No. 3, Jun. 9, 1999, pp. 257-270.
Kopreski et al., "Circulating RNA as a tumor marker", Clinical Chemistry, vol. 47, No. 2, p. 362, Feb. 2000.
Myers et al., "Isolation of a cDNA Encoding 5T4 Oncofetal Trophoblast Glycoprotein" J. Biol. Chem 269 9319-9324 (1994).
Wieczorek et al., "Diagnostic and Prognostic Value of RNA-Proteolipid in Sera of Patients with Malignant Disorders following Therapy: First Clinical Evaluation of a Novel Tumor Marker" Cancer Research 47:6407-6412 (Dec. 1, 1987).
Poon et al., "Presence of fetal RNA in maternal plasma," Clin. Chem. 47:363, Abstract No. 11, (2001).

(Continued)

*Primary Examiner*—Frank W Lu
(74) *Attorney, Agent, or Firm*—McDonnell Boehnen Hulbert & Berghoff

(57) ABSTRACT

This invention provides methods for detecting the presence of malignant or premalignant cells, or trophoblastic cells in a human wherein the malignant, premalignant or trophoblastic cells express 5T4. The methods of the invention detect 5T4 RNA in blood, blood plasma, serum, and other bodily fluids. The inventive methods are useful for detection, diagnosis, monitoring, treatment, or evaluation of neoplastic disease, and for the detection and evaluation of placental tissue in pregnant women.

3 Claims, No Drawings

OTHER PUBLICATIONS

Poon et al., "Presence of Fetal RNA in Maternal Plasma" Clin. Chem. 46:1832-1834(2000).

Kamm and Smith, "Nucleic Acid Concentrations in Normal Human Plasma," Clinical Chemistry 18(6)519-22 (1972).

El-Hefnawy et al., "Characterization of Amplifiable, Circulating RNA in Plasma and Its Potential as a Tool for Cancer Diagnostics," Clinical Chemistry 50(3)564-73 (2004).

Ng et al., "mRNA of placental origin is readily detectable in maternal plasma," PNAS 100(8)4748-53 (Apr. 15, 2003).

Tsui et al., "Stability of Endogenous and Added RNA in Blood Specimens, Serum, and Plasma," Clinical Chemistry 48 (10)1647-53 (2002).

Zhou et al., "Circulating RNA as a novel tumor marker: An in vitro study of the origins and characteristics of extracellular RNA," Cancer Letters 259:50-60 (2008).

Bianchi et al. (1991), Am. J. Path. 138(2): 279-284.

Datta et al. (1994), Journal of Clinical Oncology 12: 475-482.

Hole et al. (1988), Br. J. Cancer 57: 239-246.

Hole et al. (1990), Int. J. Cancer 45: 179-184.

Jones et al. (1990), Br. J. Cancer 61: 96-100.

Mulder et al. (1997), Clin. Cancer Res. 3: 1923-1930.

Southall et al. (1990), Br. J. Cancer 61: 89-95.

Starzynska et al. (1992), Br. J. Cancer 66: 867-869.

Starzynska et al. (1994), Br. J. Cancer 69: 899-902.

Office Action, Non-Final Rejection mailed on Oct. 24, 2006 for U.S. Appl. No. 10/363,023.

Office Action, Non-Final Rejection mailed on May 17, 2007 for U.S. Appl. No. 10/363,023.

Office Action, Non-Final Rejection mailed on Feb. 6, 2008 for U.S. Appl. No. 10/363,023.

Office Action, Final Rejection mailed on Sep. 3, 2008 for U.S. Appl. No. 10/363,023.

Office Action, Non-Final Rejection mailed on Jun. 30, 2006 for U.S. Appl. No. 10/616,210.

Office Action, Final Rejection mailed on Mar. 21, 2007 for U.S. Appl. No. 10/616,210.

Office Action, Non-Final Rejection mailed on Oct. 6, 2008 for U.S. Appl. No. 11/415,968.

Office Action, Non-Final Rejection mailed on Nov. 7, 2000 for U.S. Appl. No. 09/649,371.

Office Action, Non-Final Rejection mailed on Apr. 20, 2001 for U.S. Appl. No. 09/649,371.

Office Action, Final Rejection mailed on Feb. 6, 2002 for U.S. Appl. No. 09/649,371.

Office Action, Non-Final Rejection mailed on Sep. 30, 2002 for U.S. Appl. No. 09/649,371.

Komeda et al. "Sensitive Detection of Circulating Hepatocellular Carcinoma Cells in Peripheral Venous Blood," Cancer, 75:2214-19 (1995).

Pfleiderer "Detection of Tumour Cells in Peripheral Blood and Bone Marrow from Ewing Tumour Patients by RT-PCR," Int. J. Cancer 64: 135-9(1995).

* cited by examiner

DETECTION OF 5T4 RNA IN PLASMA AND SERUM

This application is a U.S. national phase application claiming priority to International Application, No. PCT/US01/26119, filed Aug. 21, 2001, which is a continuation-in-part of U.S. Ser. No. 09/649,371, filed Aug. 28, 2000, now U.S. Pat. No. 6,794,135 B1, issued on Sep. 21, 2004, which is a continuation-in-part of Ser. No. 09/155,152, filed Sep. 22, 1998, now U.S. Pat. No. 6,329,179 B1, issued Dec. 11, 2001.

BACKGROUND OF THE INVENTION

1. Field of the Invention

This invention relates to methods for detecting ribonucleic acid (RNA) in bodily fluids such as blood plasma and serum obtained from an animal. Specifically, the invention is directed towards methods for detecting RNA in bodily fluids from a human bearing a premalignant lesion or a malignancy, ranging from localized neoplasia to metastatic disease. The methods of the invention are particularly drawn to detecting mRNA encoding all or a portion of a particular gene, referred to herein as the 5T4 gene. This gene is expressed in many malignant and premalignant tissues, as well as in placental tissue. Since RNA is essential for expressing the 5T4 gene and producing 5T4 protein, detection and monitoring of 5T4 mRNA provides a convenient and reliable method for assessing and monitoring 5T4 gene expression.

2. Background of the Related Art

Pathogenesis and regulation of cancer is dependent upon the translation of RNA to produce proteins involved with a variety of cellular processes, such as cell proliferation, regulation, and death. Particular RNAs involved in these cellular processes include 5T4 RNA; these RNAs are associated with cellular processes characteristic of cancer, such as metastatic potential, invasiveness, and alterations of cell-cell interactions. Furthermore, some RNA and their translated proteins, although not necessarily involved in specific neoplastic pathogenesis or regulation, may serve to delineate recognizable characteristics of particular neoplasms by either being elevated or inappropriately expressed.

The 5T4 protein encoded by said RNA is a transmembrane glycoprotein normally present in trophoblast tissue whose gene structure has recently been characterized (Hole & Stem, 1988, *Br. J. Cancer* 57: 239-246; Hole & Stern, 1990, *Int. J. Cancer* 45: 179-184; Myers, 1994, *J. Biol. Chem.* 269: 9319-9324; King et al., 1999, *Biochimica et Biophysica Acta* 1445: 257-270). The protein is expressed at low levels in cells of only a few other normal epithelia. Significantly, 5T4 expression is upregulated in cells comprising many cancers and premalignant tissues, including but not limited to cancers of breast, ovary, lung, cervix, colorectum, stomach, pancreas, bladder, endometrium, brain, kidney, and esophagus (Jones et al., 1990, *Br. J. Cancer* 61: 96-100; Southall et al., 1990, *Br. J. Cancer* 61: 89-95; Starzynska et al., 1992, *Br. J. Cancer* 66: 867-869; Starzynska et al., 1994, *Br. J. Cancer* 69: 899-902). Because of this, 5T4 mRNA is considered herein to be a tumor-associated RNA. Overexpression of 5T4 is particularly associated with cancers of high metastatic potential and poorer prognosis (Mulder et al., 1997, *Clin. Cancer Res.* 3: 1923-1930; Starzynska et al., 1994, ibid.). Detection of 5T4 thereby permits detection and monitoring of a wide spectrum of cancers and premalignancies, and may have prognostic significance. 5T4 further provides a target for cancer therapies, particularly monoclonal antibody-based therapies and vaccine therapies.

RNAs associated with cancer and premalignancy have been characterized as tumor-derived, and are termed "tumor-associated RNA" herein. Co-owned and co-pending U.S. patent application Ser. No. 09/649,371, incorporated by reference herein in its entirety, provides methods for detecting tumor-associated or tumor-derived 5T4 RNA in bodily fluids such as blood plasma and serum, wherein said RNA detection is used for the detection, monitoring, or evaluation of cancer or premalignant conditions.

Another biological phenomenon in which RNA and translated proteins therefrom are fundamentally involved is the cascade of events that occur during pregnancy. Such RNAs assist in the rapid growth of specific tissues during pregnancy, being principally those of the embryo and those of the placenta, wherein placental tissue includes fetal trophoblast tissue. 5T4 is normally present in fetal trophoblast tissue, so that detection of 5T4 RNA in bodily fluids such as blood, including blood plasma and serum, from pregnant or recently pregnant women, enables the monitoring of placental conditions and states in these women, both normal and pathologic. Examples where such monitoring would be advantageous include but are not limited to monitoring of placental growth during pregnancy, evaluation of deleterious conditions associated with pregnancy such as preeclampsia and eclampsia, evaluation for retained placenta following normal delivery or following spontaneous or incomplete abortions or medical terminations of pregnancy, and monitoring of gestational trophoblastic diseases. In contradistinction with the invention disclosed herein, which enables detection of RNA specific for the trophoblastic (placental) compartment of conception rather than the entire fetal compartment (including the embryonic compartment), the presence of fetal RNA in blood plasma has recently been described (Poon et al., 2001, *Clin. Chem.* 47: 363, Abst. No. 11).

5T4 RNA being recognized herein as a tumor-associated RNA, there is a heretofore unappreciated need in the art to identify premalignant or malignant states characterized by 5T4 in a human by detecting 5T4 RNA in bodily fluids such as blood plasma or serum. Similarly, since 5T4 is a normal trophoblastic protein, a blood test for 5T4 mRNA in pregnant or recently pregnant women without cancer would be useful for diagnosing complications of pregnancy.

SUMMARY OF THE INVENTION

The present invention provides methods for evaluating a non-pregnant animal, most preferably a human, for premalignant or malignant states, disorders, or conditions, and further describes methods for evaluating a pregnant or recently pregnant woman for placental disorders or conditions, including the existence of the pregnancy per se. The inventive methods comprise detecting 5T4 RNA in bodily fluids, preferably blood and most preferably blood plasma and serum, as well as in other bodily fluids, preferably urine, effusions, ascites, amniotic fluid, saliva, cerebrospinal fluid, cervical, vaginal, and endometrial secretions, gastrointestinal secretions, bronchial secretions, breast fluid, and associated tissue washings and lavages.

In preferred embodiments, the methods of the invention comprise the step of amplifying and detecting extracellular 5T4 RNA from bodily fluids of an animal, most preferably a human.

In particularly preferred embodiments, the present invention provides methods for detecting 5T4 RNA in blood or a blood fraction, including plasma and serum, and other bodily fluids, the method comprising the steps of extracting RNA from blood, plasma, serum, or other bodily fluid, in vitro amplifying 5T4 mRNA or its cDNA, and detecting the amplified product of 5T4 mRNA or its cDNA.

In a first aspect of this embodiment, the present invention provides methods for detecting 5T4 RNA in blood or blood fractions, including plasma and serum, in an animal, most preferably a human. Said methods are advantageously provided for detecting, diagnosing, monitoring or evaluating proliferative disorders, particularly stages of neoplastic disease, including premalignancy, early cancer, non-invasive cancer, carcinoma in-situ, invasive cancer, metastatic cancer and advanced cancer, as well as benign neoplasms. In this aspect, the method comprises the steps of extracting RNA from blood or blood plasma or serum, in vitro amplifying qualitatively or quantitatively a fraction of the extracted RNA or the corresponding cDNA wherein said fraction comprises 5T4 RNA, and detecting the amplified product of 5T4 RNA or its cDNA.

The invention in a second aspect provides methods for detecting 5T4 RNA in any bodily fluid. Preferably, said bodily fluid is whole blood, blood plasma, serum, urine, effusions, ascitic fluid, amniotic fluid, saliva, cerebrospinal fluid, cervical secretions, vaginal secretions, endometrial secretions, gastrointestinal secretions, bronchial secretions including sputum, secretions or washings from the breast, and other associated tissue washings from an animal, most preferably a human. In this aspect, the method comprises the steps of extracting RNA from the bodily fluid, in vitro amplifying 5T4 RNA comprising a fraction of the extracted RNA or preferably the corresponding cDNA into which the RNA is converted in a qualitative or quantitative fashion, and detecting the amplified product of 5T4 RNA or cDNA.

In these embodiments, the inventive methods are particularly advantageous for detecting, diagnosing, monitoring, or evaluating various proliferative disorders in a non-pregnant animal, most preferably a human, particularly stages of neoplastic disease, including premalignancy, early cancer, non-invasive cancer, carcinoma-in-situ, invasive cancer, metastatic cancer and advanced cancer as well as benign neoplasm.

The invention also provides methods for detecting, diagnosing, monitoring, or evaluating pregnancy and placental disorders and conditions in a woman having a current or antecedent pregnancy, particularly disorders and conditions characterized by or associated with trophoblast tissue including placental insufficiency, preeclampsia, eclampsia, gestational trophoblastic diseases such as molar pregnancy, gestational trophoblastic neoplasia, and conditions associated with inappropriately retained trophoblastic tissue, such as following labor and delivery, and following recognized or unrecognized early terminations of the pregnancy, such as in spontaneous or incomplete abortions or following medical termination of the pregnancy.

The methods of the invention are additionally useful for identifying 5T4 RNA-expressing cells or tissue in an animal, most preferably a human. In these embodiments, detection of an in vitro amplified product of 5T4 RNA using the methods of the invention indicates the existence of 5T4-expressing cells or tissue in a human.

The invention advantageously provides oligonucleotide primers useful in the efficient amplification of 5T4 mRNA or cDNA from bodily fluid, most preferably blood plasma or serum.

The invention further provides diagnostic kits for detecting 5T4 RNA in bodily fluid, preferably blood plasma or serum, wherein the kit comprises oligonucleotide primers, probes, or both primers and probes for amplifying and/or detecting 5T4 RNA or cDNA derived therefrom.

In preferred embodiments of the inventive methods, 5T4 RNA is extracted from whole blood, blood plasma or serum, or other bodily fluids using an extraction method such as gelatin extraction method; silica, glass bead, or diatom extraction method; guanidinium thiocyanate acid-phenol based extraction methods; guanidinium thiocyanate acid based extraction methods; methods using centrifugation through cesium chloride or similar gradients; phenol-chloroform based extraction methods; or other commercially available RNA extraction methods. Extraction may alternatively be performed using one or a multiplicity of probes that specifically hybridize to 5T4 RNA.

In preferred embodiments of the inventive methods, 5T4 RNA or cDNA derived therefrom is amplified using an in vitro amplification method such as reverse transcriptase polymerase chain reaction (RT-PCR); ligase chain reaction; DNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; or any combination or variation thereof.

In preferred embodiments of the inventive methods, detecting an amplification product of 5T4 RNA or 5T4 cDNA is accomplished using a detection method such as gel electrophoresis; capillary electrophoresis; conventional enzyme-linked immunosorbent assay (ELISA) or modifications thereof, such as amplification using biotinylated or otherwise modified primers; nucleic acid hybridization using specific labeled probes, such as fluorescent-, radioisotope-, or chromogenically-labeled probe; Southern blot analysis; Northern blot analysis; electrochemiluminescence; laser-induced fluorescence; reverse dot blot detection; and high-performance liquid chromatography.

In particularly preferred embodiments of the inventive methods, 5T4 RNA is converted to cDNA using reverse transcriptase after extraction of RNA from a bodily fluid and prior to amplification.

The methods of the invention are advantageously used for providing a diagnosis or prognosis of, or as a predictive indicator for determining risk for a human for developing a proliferative, premalignant, neoplastic, or malignant disease comprising or characterized by the existence of cells expressing 5T4 RNA.

The methods of the invention are particularly useful for providing a diagnosis of or for identifying in non-pregnant animals, particularly humans, individuals at risk for developing or who have developed malignancy or premalignancy of the cells comprising epithelial tissues. Most preferably, malignant or premalignant diseases, conditions, or disorders advantageously detected or diagnosed using the methods of the invention are breast, ovarian, lung, cervical, colorectal, gastric, pancreatic, bladder, endometrial, kidney, and esophageal cancers, and premalignancies and carcinoma in-situ such as cervical dysplasia, cervical intraepithelial neoplasia (CIN), bronchial dysplasia, atypical hyperplasia of the breast, ductal carcinoma in-situ, colorectal adenoma, atypical endometrial hyperplasia, and Barrett's esophagus, and further gestational trophoblastic cancers and gestational trophoblastic disease in woman with a recent antecedent pregnancy.

In certain preferred embodiments of the methods of the invention, 5T4 RNA or cDNA derived therefrom is amplified in a quantitative manner, thereby enabling comparison of amounts of 5T4 RNA present in a bodily fluid such as blood plasma or serum from a human. In these embodiments, the amount of extracellular 5T4 RNA detected in an individual is compared with a range of amounts of extracellular 5T4 RNA detected in said bodily fluid in populations of humans known to have a premalignant or malignant disease, or known to be free from a premalignant or malignant disease.

In alternative embodiments, said quantitative detection of 5T4 RNA in bodily fluids in an animal, most preferably a human, is provided for comparing the amount of 5T4 RNA in said bodily fluid in pregnant individuals that have a normal placenta, or that have placental disorders and conditions, particularly disorders and conditions characterized by or associated with trophoblast tissue including placental insufficiency, preeclampsia, eclampsia, gestational trophoblastic diseases such as molar pregnancy, gestational trophoblastic neoplasia, and conditions associated with inappropriately retained trophoblastic tissue, such as following labor and delivery, and following recognized or unrecognized early terminations of the pregnancy, such as in spontaneous or incomplete abortions or following medical termination of the pregnancy.

The methods of the invention further provide methods for identifying individuals having a 5T4 expressing malignancy or premalignancy, thereby permitting rational, informed treatment options to be used for making therapeutic decisions. In particular, the methods of the invention are useful in identifying individuals having a premalignancy or malignancy that would benefit from a 5T4-directed therapy, such as monoclonal antibody therapy, anti-sense therapy, and vaccine therapy.

Another advantageous aspect of the methods of the invention is as a marker for monitoring or assessing the adequacy of anticancer therapy, including surgical intervention, chemotherapy, biotherapy such as monoclonal antibody therapy or vaccines, and radiation therapy, or for determining whether additional or more advanced therapy is required. The invention therefore provides methods for monitoring the response to treatment in such patients and for developing a prognosis in such patients.

The methods of the invention also allow identification or analysis of 5T4 RNA, either qualitatively or quantitatively, in the blood or other bodily fluid of an animal, most preferably a human that has completed therapy, as an early indicator of relapsed cancer, impending relapse, or treatment failure.

The invention provides methods for monitoring trophoblast RNA in plasma or serum or other bodily fluids during a pregnancy. The methods of the invention thereby permit placental monitoring in a pregnant woman, wherein quantitative evaluations of plasma or serum 5T4 RNA are most preferably made serially during a pregnancy, or wherein a single quantitative evaluation of 5T4 RNA is compared to the normal serum or plasma 5T4 RNA values among females, most preferably women, having healthy pregnancies. The invention provides methods for comparing blood levels of RNA derived from the trophoblast to blood levels of RNA derived from the embryo and/or blood levels of RNA derived from maternal cells.

The methods of the invention also permit detection of retained placental tissue in a woman following labor and delivery, or following early termination of a pregnancy such as in spontaneous or incomplete abortions (i.e., miscarriages).

Specific preferred embodiments of the present invention will become evident from the following more detailed description of certain preferred embodiments and the claims.

DETAILED DESCRIPTION OF THE PREFERRED EMBODIMENTS

The invention provides methods for detecting 5T4 RNA in bodily fluids in an animal, most preferably a human, and thereby enables detection of cancerous or precancerous cells. The invention also provides methods for detecting placental tissues that express 5T4, thereby permitting detection of pregnancy and complications or conditions incident to pregnancy.

In preferred embodiments of the methods of the invention, extracellular RNA particularly comprising 5T4 RNA is extracted from a bodily fluid. This extracted RNA is then amplified, either after conversion into cDNA or directly, using in vitro amplification methods in either a qualitative or quantitative manner, and using oligonucleotide primers specific for 5T4 RNA or cDNA. The amplified product is then detected in either a qualitative or a quantitative manner.

In the practice of the methods of the invention, 5T4 RNA may be extracted from a bodily fluid, including but not limited to whole blood, plasma, serum, urine, effusions, ascitic fluid, saliva, cerebrospinal fluid, cervical secretions, vaginal secretions, endometrial secretions, amniotic fluid, gastrointestinal secretions, bronchial secretions including sputum, breast fluid or secretions or washings. Extraction can be performed using, for example, extraction methods described in co-owned and co-pending U.S. patent application Ser. No. 09/155,152, the entire disclosure of which is hereby incorporated by reference. In a preferred embodiment, the bodily fluid is either blood plasma or serum. It is preferred, but not required, that blood be processed soon after drawing, and preferably within three hours, to minimize any degradation in the sample. In a preferred embodiment, blood is first collected by venipuncture and kept on ice until use. Preferably within 30 minutes of drawing the blood, serum is separated by centrifugation, for example at 1100× g for 10 minutes at 4 degrees centigrade. When using plasma, blood should not be permitted to coagulate prior to separation of the cellular and acellular, blood components. Serum or plasma can be frozen until use, for example at −70 degrees centigrade after separation from the cellular portion of blood. When using frozen blood plasma or serum, the frozen plasma or serum is rapidly thawed, for example in a water bath at 37 degrees centigrade, and RNA is extracted therefrom without undue delay, most preferably using a commercially available kit (for example the Perfect RNA Total RNA Isolation Kit obtained from Five Prime—Three Prime, Inc., Boulder, Colo.), according to the manufacturer's instructions. Other alternative and equivalent methods of RNA extraction are further provided in co-owned and, co-pending U.S. patent application Ser. No. 09/155,152, incorporated herein by reference in its entirety.

Following extraction of RNA from a bodily fluid that contains 5T4 mRNA, the 5T4 mRNA or cDNA derived therefrom is amplified in vitro. Applicable amplification assays are detailed in co-owned and co-pending U.S. patent application Ser. No. 09/155,152, as herein incorporated by reference, and include but are not limited to reverse transcriptase polymerase chain reaction (RT-PCR), ligase chain reaction, DNA signal amplification, amplifiable RNA reporters, Q-beta replication, transcription-based amplification, boomerang DNA amplification, strand displacement activation, cycling probe technology, isothermal nucleic acid sequence based amplification, and other self-sustained sequence replication assays.

In preferred embodiments of the methods of the invention, 5T4 mRNA is converted into cDNA using reverse transcriptase prior to in vitro amplification using methods known in the art. For example, a sample such as 10 microliters (microL) extracted serum RNA is reverse-transcribed in a 30 microL volume containing 200 Units of Moloney murine leukemia virus (MMLV) reverse transcriptase (Promega, Madison, Wis.), a reaction buffer supplied by the manufacturer, 1 mM each dNTPs, 0.5 micrograms random hexamer oligonucleotide primers, and 25 Units of RNAsin (Promega, Madison, Wis.). Reverse transcription is typically performed under an overlaid mineral oil layer to inhibit evaporation, and incubated at room temperature for 10 minutes followed by incubation at 37 degrees C. for one hour.

Amplification oligonucleotide primers are selected to be specific for amplifying 5T4 nucleic acid. In a preferred embodiment, amplification is performed by RT-PCR. In this embodiment, preferred oligonucleotide primers have a nucleotide sequence as follows:

Primer 5T4-1: TCTTCGCCTCTTGTTGGC (gene location exon 2, 5T4 gene; Genbank accession #HSA012159; SEQ ID No. 1)

Primer 5T4-2: TGCAGGAAGGAACGGGA (gene location exon 1, 5T4 gene; Genbank accession #HSA012159; SEQ ID No. 2)

Primer 5T4-3: TTGGTAGGGAAGGAATTGGG (gene location exon 1, 5T4 gene; Genbank accession #HSA012159; SEQ ID No. 3)

Primer 5T4-1 and Primer 5T4-2 are particularly useful because they span the first intron and are therefore specific for cDNA and will not amplify contaminating genomic DNA (if any is present).

In one example of a preferred embodiment, 5T4 RNA is harvested from serum or plasma, and RNA extracted therefrom by the Perfect RNA Total RNA Isolation Kit (Five Prime—Three Prime, Inc., Boulder, Colo.) according to manufacturer's instructions. A sample of this extracted RNA preparation is reverse transcribed to cDNA, and RT-PCR for the 5T4 cDNA performed using the primers described above. The cDNA is amplified in a single-stage reaction in a thermocycler under a temperature profile that produces the specific fragment; typically, such a thermocycling profile consists of an initial 10 minute incubation at 95 degrees C., followed by about 45 cycles of denaturation at 94 degrees C. for 30 seconds, annealing at 57 degrees C. for 30 seconds, and extension at 72 degrees C. for 30 seconds, followed by a final incubation at 72 degrees C. for 8 minutes. Detection of the amplified product is achieved, for example by gel electrophoresis through a 5% Tris-borate-EDTA (TBE) agarose gel, using ethidium bromide staining for visualization and identification of the product fragment. The expected size of the product fragment is 101 base pairs in length.

In a particularly preferred embodiment, 5T4 cDNA is amplified by RT-PCR in a hemi-nested, two stage amplification reaction. In this embodiment, the reaction mixture and amplification in the first stage are identical to that of the single stage RT-PCR reaction described above, except that the reaction mixture for the first stage utilizes only 1 picomole each of above-identified Primer 5T4-1 and Primer 5T4-2, and thermocycling during the first stage is performed using an otherwise identical temperature profile to the single stage method but for only 25 cycles. Following the first stage amplification, one-tenth volume of each reaction mixture is transferred to fresh tubes, and a new reaction mixture is prepared that is identical to the mixture described above except that 10 picomoles each of Primer 5T4-1 and Primer 5T4-3 described above are utilized. The reaction mixture is then reamplified in a thermocycler for 35 additional cycles under the above-described temperature profile. Detection of the amplified product fragment is achieved as described above, with the amplified product fragment being 73 base pairs long.

In alternative preferred embodiments, amplified products can be detected using other methods, including but not limited to other gel electrophoresis methods; capillary electrophoresis; ELISA or modifications thereof, such as amplification using biotinylated or otherwise modified primers; nucleic acid hybridization using specific, detectably-labeled probes, such as fluorescent-, radioisotope-, or chromogenically-labeled probes; Southern blot analysis; Northern blot analysis; electrochemiluminescence; laser-induced fluorescence; reverse dot blot detection; and high-performance liquid chromatography. Furthermore, PCR product fragment detection may be performed in either a qualitative or quantitative fashion.

PCR product fragments produced using the methods of the invention can be further cloned into recombinant DNA replication vectors using standard techniques. RNA can be produced from cloned PCR products, and in some instances the RNA expressed thereby, for example, using the TnT Quick Coupled Transcription/Translation kit (Promega, Madison, Wis.) as directed by the manufacturer.

In another embodiment, restriction digestion may be performed upon the single-stage RT-PCR product with BamHI yielding two fragments of approximately 67 and 34 bp. The products of the restriction digestion can be further amplified in a second stage amplification reaction using appropriate primers.

In a preferred embodiment, 5T4 mRNA is amplified in a quantitative fashion thereby enabling comparison of the amount of extracellular 5T4 mRNA in an individual's bodily fluid with the range of amounts of 5T4 mRNA present in the bodily fluids of populations with cancer, premalignancy, pregnancy, recent pregnancy, or non-pregnant normal populations.

The methods of the invention as described above is not limited to blood plasma or serum, and can be performed in like manner for detecting 5T4 mRNA from other bodily fluids, including but not limited to whole blood, urine, effusions, ascitic fluid, saliva, cerebrospinal fluid, cervical secretions, vaginal secretions, endometrial secretions, amniotic fluid, gastrointestinal secretions, breast fluid or secretions, and bronchial secretions including sputum. Although fractionation of the bodily fluid into its cellular and non-cellular components is not required for the practice of the invention, the non-cellular fraction may be separated, for example, by centrifugation or filtration of the bodily fluid.

The methods of the invention are useful in the practice of diagnostic methods for detecting 5T4 mRNA in an animal, most preferably a human at risk for developing or who has developed a premalignant or malignant neoplastic disease comprising cells expressing 5T4 mRNA. The invention further provides a method of identfying animals, particularly humans who are at risk for developing, or who have developed premalignancies or cancer of epithelial tissues and components of tissues, including but not limited to breast, ovarian, lung, cervical, colorectal, gastric, pancreatic, bladder, endometrial, kidney, and esophageal cancers, as well as premalignancies and carcinoma in-situ including but not limited to cervical dysplasia and cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The diagnostic methods of the invention can be advantageously performed using a diagnostic kit as provided by the invention, wherein the kit includes oligonucleotide primers specific for 5T4 cDNA synthesis or in vitro amplification or both, and/or specific probes, most preferably oligonucleotide probes for detecting 5T4 RNA or cDNA or in vitro amplified DNA fragments thereof. The kit may further include methods and reagents for extracting 5T4 RNA from a bodily fluid, wherein the bodily fluid is most preferably but not limited to blood plasma or serum.

The inventive methods have significant advantages in assigning and monitoring therapies not specifically directed at 5T4 expressing cells, including chemotherapy, radiation therapy, and surgery, as well as 5T4-specific or directed therapies such as 5T4-directed monoclonal antibody therapy and 5T4-directed vaccine therapy. The methods of the invention permit stratification and selection of individuals, particularly individual human patients likely to benefit from 5T4-specific or directed therapy. The inventive methods are also useful for monitoring response, relapse, and prognosis of 5T4-producing neoplastic disease. Of particular value, the invention allows a determination that a 5T4-directed therapy is therapeutically indicated even in cases of premalignancy, early cancer, or occult cancers or minimum residual disease, as well as when metastatic disease is present. Thus, the invention permits therapeutic intervention when tumor burden is low, immunologic function is relatively intact, and the patient is not compromised, all increasing the potential for cure.

The methods of the invention further enable 5T4 RNA to be evaluated in blood plasma, serum or other bodily fluid in combination with detection of other tumor-associated or tumor-derived RNA or DNA in a concurrent or sequential fashion, such as in a multiplexed assay or in a chip-based assay, thereby increasing the sensitivity or efficacy of the assay in the detection or monitoring of neoplastic disease. For example, but not as a limitation, 5T4 RNA can be detected in blood, plasma, serum, or other bodily fluid in combination with detection of telomerase-associated RNA such as hTR and/or hTERT, or in combination with detection of human papillomavirus DNA.

The invention also provides methods for detecting 5T4 RNA in pregnant animals, most preferably pregnant women, and thereby provides a method of monitoring the competency and health of the placenta. The amount of 5T4 RNA present in blood plasma or serum of a pregnant woman generally corresponds to the amount of placental tissue present, the health of the placenta, and duration of pregnancy. Quantitative serial determinations of 5T4 RNA in blood plasma and serum thereby enable non-invasive assessment and monitoring of the placenta during pregnancy. Comparison of quantitative values of plasma or serum 5T4 RNA (or other trophoblastic RNA) within a particular pregnant woman to a normal range within healthy pregnancies at any given stage of pregnancy, or in comparison to embryonic development, can be utilized to indicate placental pathology, such as may occur in preeclampsia, eclampsia, and placental insufficiency, and the appropriateness of medical intervention.

While the placenta is normally delivered completely following labor, in some cases the placenta or portions thereof may be retained with potential deleterious consequences to the woman. Trophoblastic tissue may be inappropriately retained post-partum, such as in association with placental accreta and placental increta, or following antecedent pregnancies, such as pregnancies characterized by blighted ovum syndrome, spontaneous or incomplete abortions (miscarriages) with retained products of conception, or following medical terminations of the pregnancy. Furthermore, trophoblastic tissue persists in gestational trophoblastic diseases, including molar pregnancy, and gestational trophoblastic neoplasia. Thus, the methods of the invention can be used to determine the presence of retained placental tissue or products of conception. In these uses of the inventive methods, persistence of trophoblastic RNA in plasma or serum in a woman with a recent antecedent pregnancy is indicative of retained trophoblastic tissue. The invention further permits detection, evaluation, and monitoring of gestational trophoblastic diseases and gestational trophoblastic neoplasia thereby.

The invention also provides methods for detecting trophoblastic tissue in a pregnant or recently pregnant woman, wherein said method comprises extracting trophoblast RNA from the blood plasma or serum of said woman, wherein the trophoblast RNA is not normally detectable at similar quantitative or qualitative levels in the blood of a healthy non-pregnant woman. It will be understood that the methods of the invention as applied to the pregnant or recently pregnant woman for detecting 5T4 RNA are applicable to any RNA that is primarily of trophoblastic origin and which is not normally detectable in blood of healthy non-pregnant woman; this application of the inventive methods requires that the nucleic acid sequence of the RNA is known to the art, permitting production of oligonucleotide primers therefore. In a preferred embodiment of the methods of the invention the trophoblast RNA species is 5T4 RNA. In other preferred embodiments of the inventive methods the trophoblast RNA species is, but is not limited to, beta-human chorionic gonadotrophin (hCG) RNA, alpha-hCG RNA, carcinoembryonic RNA (CEA RNA), placental alkaline phosphatase RNA (PLAP RNA), and pregnancy-specific glycoprotein RNA (PSG RNA). Furthermore, multiple trophoblast RNA species may be evaluated from plasma or serum in a concurrent or sequential fashion, such as in a multiplexed assay or in a chip-based assay.

The methods of the invention and preferred uses for the methods of the invention are more fully illustrated in the following Examples. These Examples illustrate certain aspects of the above-described method and advantageous results. These Examples are shown by way of illustration and not by way of limitation.

Example 1

Detection of 5T4 mRNA in Placental and Carcinoma Tissue

5T4 mRNA was detected in placental tissue and other normal and cancerous human tissues as follows. Normal placenta was obtained within hours of delivery and stored at −80 degrees C. until use. Normal human tissues from other organs, consisting of normal tissue from brain, kidney, liver, skeletal muscle, spleen, and myocardium, were obtained from autopsies within 12 hours of death, snap frozen, and stored at −80 degrees C. until use. In addition, eight human breast cancer specimens and sixteen human lung cancer specimens were available as formalin-fixed, paraffin-embedded tissue obtained at times of biopsy or surgery.

Placental RNA and RNA from normal tissues of the brain, kidney, liver, skeletal muscle, spleen and myocardium were extracted from five 20 micron slices of each fresh tissue sample using the Perfect RNA Total RNA Isolation kit (Five Prime—Three Prime, Inc., Boulder Colo.), according to manufacturer's instructions. For each tissue specimen, extracted RNA was then reverse transcribed to cDNA in a 30 microL volume containing 200 Units of Moloney murine leukemia virus (MMLV) reverse transcriptase (Promega, Madison, Wis.), a reaction buffer supplied by the manufacturer, 1 mM each dNTPs, 0.5 micrograms random hexamer oligonucleotide primers, and 25 Units of RNAsin (Promega, Madison, Wis.). Reverse transcription was performed under an overlaid mineral oil layer to inhibit evaporation, and incubated at room temperature for 10 minutes followed by incubation at 37 degrees C. for one hour. RT-PCR was then performed as either a single-stage amplification or as a two-stage, hemi-nested amplification, wherein for the single-stage amplification, 5 microliters of the 5T4 cDNA was used in a final volume of 50 microL in a reaction mixture containing 1U of Amplitaq Gold (Perkin Elmer Corp., Foster City, Calif.), 1× reaction buffer supplied with Amplitaq by the manufacturer, 1.5 mM $MgCl_2$, 200 microM each dNTP, and 10 picomoles each of Primer 5T4-1 and Primer 5T4-2 identified above. The mixture was amplified in a single-stage reaction in a thermocycler under a temperature profile consisting of an initial 10 minute incubation at 95 degrees C., followed by 45 cycles of denaturation at 94 degrees C. for 30 seconds, annealing at 57 degrees C. for 30 seconds, and extension at 72 degrees C. for 30 seconds, followed by a final incubation at 72 degrees C. for 8 minutes. The amplified product (101 bp) was detected by gel electrophoresis through a 5% agarose gel with staining of products by ethidium bromide for identification of the product. From the placental tissue specimens, a 5T4-specific RT-PCR product was produced, indicating that 5T4 mRNA was present in the placenta. For the two-stage, hemi-nested RT-PCR amplification reactions, the reaction mixture and amplification in the first stage were identical to that of the single-stage RT-PCR reaction described, except that only 1 picomole each of Primer 5T4-1 (SEQ ID No. 1) and Primer 5T4-2 (SEQ ID No. 2) were used, and thermocycling was performed for only 25 cycles. Following the first stage amplification, one-tenth of the reaction mixture was transferred to fresh tubes, and a new reaction mixture was prepared that was the same as the previous mixture except for the primers, wherein 10 picomoles each of Primer 5T4-1 (SEQ ID No. 1) and Primer 5T4-3 (SEQ ID No. 3) as previously described were used. The reaction mixture was then reamplified for 35 additional cycles at the above temperature profile. The 5T4 amplified product fragment from placenta was detected by gel electrophoresis through a 5% agarose gel, with staining of products by ethidium bromide for identification of the product, with the expected amplified product being 73 base pairs long. In comparison, of all samples of normal tissue from which RNA was prepared, none of the autopsy tissues contained amplifiable 5T4 mRNA. As a positive control, c-abl mRNA in these tissues could be demonstrated by PCR amplification using c-abl specific primers.

5T4 mRNA was detected in human tumor samples as follows. Formalin-fixed cancer tissues were used, with RNA prepared from two 10 micron slices of each paraffin-embedded lung and breast cancer specimen, processed according to the method of Bianchi et al. (1991, *Am. J. Path.* 138: 279-284), with the exception that harvested RNA was used directly (5 or 18 microliters of 500 microliters total after organic extractions) for reverse transcription rather than following ethanol precipitation. The extracted RNA was then amplified by RT-PCR, using the protocol described above using either a single-stage or two-stage PCR assay. Amplified products were detected by gel electrophoresis through a 5% agarose gel and visualized by staining with ethidium bromide for identification of the products. 5T4 mRNA amplified products were detectable by gel electrophoresis in 3 lung cancer specimens, and in 3 breast cancer specimens, indicating the presence of 5T4 mRNA in these specimens.

Example 2

Detection of 5T4 mRNA in Serum From Cancer Patients

Sera were prepared from the blood of 5 patients with breast cancer and 14 patients with lung cancer in the manner described above. Blood was kept on ice following venipuncture and serum was separated within 30 min of blood draw by centrifugation at 1100× g for 10 minutes at 4 degrees C., and then the serum was stored frozen at −70 degrees C. until assayed. At the time of assay, the sera were rapidly thawed by placing serum samples in a water bath heated to 37 degrees C. RNA was then extracted from 1.75 mL of sera using the Perfect RNA Total RNA Isolation Kit (Five Prime-Three Prime, Inc., Boulder, Colo.) according to the manufacturer's instructions. Ten microL of the extracted RNA was then reverse transcribed using MMLV reverse transcriptase (Promega, Madison, Wis.) in the manner described above, wherein 10 microL of extracted serum RNA was reverse-transcribed in a 30 microL volume containing 200 Units of MMLV reverse transcriptase (Promega), a reaction buffer supplied by the manufacturer, 1 mM each dNTPs, 0.5 micrograms random hexamer mixture of oligonucleotide primers, and 25 Units of RNAsin (Promega), with incubation at room temperature for 10 minutes followed by incubation at 37 degrees C. for one hour. The 5T4 cDNA was then amplified by PCR using the primers and amplification parameters as described in Example 1 either by single stage or two stage, hemi-nested RT-PCR amplification. All specimens were evaluated by the single stage PCR amplification, and then separately evaluated using the more sensitive two-stage, hemi-nested PCR amplification reaction. For the single-stage amplification, 5 microliters of the 5T4 cDNA was used in a final volume of 50 microL in a reaction mixture containing 1U of Amplitaq Gold (Perkin Elmer Corp., Foster City, Calif.), 1× reaction buffer, 1.5 mM $MgCl_2$; 200 microM each dNTPs, and 10 picomoles each of Primer 5T4-1 (SEQ ID No. 1) and Primer 5T4-2 (SEQ ID No 2). The mixture was amplified in a single-stage reaction in a thermocycler under a temperature profile consisting of an initial 10 minute incubation at 95 degrees C., followed by 45 cycles of denaturation at 94 degrees C. for 30 seconds, annealing at 57 degrees C. for 30 seconds, and extension at 72 degrees C. for 30 seconds, followed by a final incubation at 72 degrees C. for 8 minutes. The amplified product was detected by gel electrophoresis through a 5% agarose gel with staining of amplified products by ethidium bromide for identification of the product. For the two-stage, hemi-nested RT-PCR amplification reactions, the reaction mixture and amplification in the first stage were identical to that of the single-stage RT-PCR reaction described above, except that only 1 picomole of Primer 5T4-1 (SEQ ID No. 1) and Primer 5T4-2 (SEQ ID No. 2) were used, and thermocycling was performed for only 25 cycles. Following the first stage amplification, one-tenth of the reaction mixture was transferred to fresh tubes, and a new reaction was prepared that was the same as the previous mixture except for the primers, wherein 10 picomoles each of Primer 5T4-1 (SEQ ID No. 1) and Primer 5T4-3 (SEQ ID No. 3) were used. The reaction mixture was then reamplified for 35 additional cycles at the above temperature profile. The 5T4 amplified product was detected by gel electrophoresis through a 5% agarose gel, with staining of products by ethidium bromide for identification of the product, with the expected amplified product being 73 base pairs in length. Two of the 19 patients, both with lung cancer, had sera positive for 5T4 mRNA using the single-stage PCR assay, while the more sensitive hemi-nested two stage PCR assay demonstrated sera to be positive for 5T4 mRNA in 8 patients, including those of 2 breast cancer patients and 6 lung cancer patients (including both patients positive with the single-stage assay). Positive and negative controls consisting of placental tissue RNA as a positive control and a cDNA absent blank as a negative control were appropriate for all reactions.

Example 3

Detection of 5T4 RNA in the Plasma of a Woman Post-Partum

A 27 year old woman delivers a healthy baby at term following a normal labor and delivery. Thirty-six hours following delivery (postpartum) the woman develops a fever, raising the clinical question of possible retained placental tissue. Plasma is drawn from the woman, and 5T4 RNA is demonstrated in her plasma at higher than expected levels using the methods as outlined in the invention. The finding of 5T4 RNA in the plasma supports the clinical suspicion of retained placental tissue, and the woman undergoes further surgical procedures.

Example 4

Detection of 5T4 RNA in the Serum of a Woman Following a Spontaneous Loss of Pregnancy A 22 year old woman in her first pregnancy suffers a spontaneous abortion (miscarriage) following 7 weeks of pregnancy. She reports heavy bleeding and passing tissues of conception, but it is unclear whether all fetal tissue has passed. Three days following the event, blood is drawn from the woman and the serum tested for the presence of 5T4 RNA using the methods of the invention. The presence of 5T4 RNA is confirmed in the woman, suggesting the presence of retained trophoblastic tissue. The woman consequently undergoes a further surgical procedure to remove the remaining tissues of conception.

Example 5

Detection of 5T4 RNA in the Serum of a Woman with Gestational Trophoblastic Disease/Neoplasia Following an Antecedent Pregnancy A 25 year old woman suffers a first trimester miscarriage. Four months following her miscarriage, serum is obtained and the methods of the invention used to demonstrate that the serum contains high levels of 5T4 RNA. A diagnosis of gestational trophoblastic disease is made and the woman treated surgically. Serum 5T4 RNA levels are quantitatively followed with a transient decline in levels. Six months following her surgical procedure, serum 5T4 RNA levels are noted to be persistently rising, and a chest x-ray demonstrates a new pulmonary lesion. Gestational trophoblastic neoplasia is suspected based upon elevated 5T4 RNA and elevated serum beta-HCG RNA levels, and the diagnosis is confirmed by biopsy. The patient subsequently is treated by chemotherapy including a 5T4-directed therapy.

Example 6

Use of Plasma 5T4 mRNA in the Monitoring of Cancer

A 42 year old man is diagnosed with renal cancer. Plasma 5T4 mRNA is quantitatively measured using the methods of the invention prior to initiation of therapy. The man then undergoes surgical resection of his renal cancer. The plasma 5T4 mRNA levels are then followed using the methods of the invention in a serial manner to aid in the determination of prognosis, relapse, and recurrence, as well as response to subsequent therapies.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of detecting an amplifiable extracellular human 5T4 RNA in blood plasma or serum from a post-partum woman without cancer, the method comprising the steps of:
   a) extracting extracellular RNA from blood plasma or serum from a post-partum woman without cancer, a portion of said extracted extracellular RNA comprising an amplifiable extracellular human 5T4 RNA;
   b) amplifying said portion of said RNA extracted from the blood plasma or serum from the post-partum woman without cancer, or cDNA prepared therefrom, wherein said portion comprises an amplifiable extracellular human 5T4 RNA, or a fragment thereof and wherein said amplifying step is performed in either a qualitative or quantitative fashion using oligonucleotide primers specific for the 5T4 RNA or cDNA, or a fragment thereof; and
   c) detecting the extracellular human 5T4 RNA or cDNA amplified according to step (b).

2. The method of claim 1, wherein the amplification in step (b) is performed by an RNA amplification method that amplifies the human 5T4 RNA directly or wherein the human 5T4 RNA is first reverse transcribed to cDNA, whereby the cDNA is amplified, wherein the amplification method is reverse transcriptase polymerase chain reaction, branched DNA signal amplification, amplification using amplifiable RNA reporters, Q-beta replication, transcription-based amplification, isothermal nucleic acid sequence based amplification, self-sustained sequence replication assays, or boomerang DNA amplification.

3. The method of claim 1, wherein said step of detecting amplified human 5T4 RNA or cDNA in step (c) is performed using gel electrophoresis, capillary electrophoresis, labeled fluorescent or chromogenic probes, laser-induced fluorescence, Southern blot analysis, Northern blot analysis, electrochemiluminescence, reverse dot blot detection, or high-performance liquid chromatography.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Homo sapiens

<400> SEQUENCE: 1
tcttcgcctc ttgttggc                                                 18

<210> SEQ ID NO 2
<211> LENGTH: 17
<212> TYPE: DNA
<213> ORGANISM: Homo sapiens

<400> SEQUENCE: 2
tgcaggaagg aacggga                                                  17

<210> SEQ ID NO 3
<211> LENGTH: 20
<212> TYPE: DNA
<213> ORGANISM: Homo sapiens
```

```
<400> SEQUENCE: 3
ttggtaggga aggaattggg                                               20
```